United States Patent
Fang et al.

(10) Patent No.: US 10,391,103 B2
(45) Date of Patent: Aug. 27, 2019

(54) FERROPORPHYRIN SOLID DISPERSION AND PREPARATION METHOD THEREOF

(71) Applicant: Sinotherapeutics Inc., Shanghai (CN)

(72) Inventors: Larry Yun Fang, Shanghai (CN); Jiansheng Wan, Shanghai (CN); Kun Li, Shanghai (CN); Maojian Gu, Shanghai (CN)

(73) Assignee: SINOTHERAPEUTICS INC., Shanghai (CN)

( * ) Notice: Subject to any disclaimer, the term of this patent is extended or adjusted under 35 U.S.C. 154(b) by 40 days.

(21) Appl. No.: 15/033,310

(22) PCT Filed: Nov. 17, 2014

(86) PCT No.: PCT/CN2014/091260
§ 371 (c)(1),
(2) Date: Apr. 29, 2016

(87) PCT Pub. No.: WO2015/074524
PCT Pub. Date: May 28, 2015

(65) Prior Publication Data
US 2016/0243130 A1 Aug. 25, 2016

(30) Foreign Application Priority Data
Nov. 22, 2013 (CN) .......................... 2013 1 0596082

(51) Int. Cl.
*A61K 31/555* (2006.01)
*A61K 9/14* (2006.01)
*A61K 9/16* (2006.01)

(52) U.S. Cl.
CPC ............ *A61K 31/555* (2013.01); *A61K 9/146* (2013.01); *A61K 9/1682* (2013.01)

(58) Field of Classification Search
CPC .................................................. A61K 31/555
See application file for complete search history.

(56) References Cited

U.S. PATENT DOCUMENTS

| 6,066,334 A * | 5/2000 | Kolter | A61K 9/2027 424/465 |
| 2003/0086976 A1* | 5/2003 | Hayes | A61K 9/146 424/486 |
| 2008/0118552 A1* | 5/2008 | Suzuki | A61K 9/146 424/451 |
| 2011/0160350 A1* | 6/2011 | Bergman | C08F 2/20 524/5 |

FOREIGN PATENT DOCUMENTS

CN 101384172 A 3/2009

OTHER PUBLICATIONS

International Search Report dated Feb. 17, 2015 in PCT/CN2014/091260.
Written Opinion dated Feb. 17, 2015 in PCT/CN2014/091260.

* cited by examiner

*Primary Examiner* — Kyle A Purdy
(74) *Attorney, Agent, or Firm* — Adsero IP (57) ABSTRACT

Disclosed are a ferroporphyrin solid dispersion, preparation method therefor and a pharmaceutical composition comprising the solid dispersion, wherein the weight ratio of ferroporphyrin to the carrier material in the dispersion is 1:1-1:10. The solid dispersion of the present invention masks the undesirable taste of ferroporphyrin, ameliorates irritation thereof to the digestive tract, and at the same time increases the solubility thereof and improves the bioavailability thereof.

23 Claims, 5 Drawing Sheets

FERROPORPHYRIN SOLID DISPERSION AND PREPARATION METHOD THEREOF

CROSS REFERENCE TO RELATED APPLICATIONS

This application is a 35 U.S.C. § 371 national phase application of PCT/CN2014/091260 (WO 2015/074524) filed on Nov. 17, 2014, entitled "Ferroporphyrin Solid Dispersion and Preparation Method Therefor", which claims the priority of Chinese Application No. 201310596082.6 filed on Nov. 22, 2013 and entitled "Ferroporphyrin solid dispersion and preparation method therefor", the entire contents of which are incorporated herein by reference.

FIELD OF THE INVENTION

The present invention relates to a solid dispersion comprising ferroporphyrin as an active ingredient, a method of preparing said solid dispersion, and a solid formulation comprising said solid dispersion.

BACKGROUND OF THE INVENTION

Iron, as an important nutritional element, is essential to human body. The deficiency or poor availability of iron might lead to disorders of metabolic processes such as transportation and storage of oxygen, transportation of carbon dioxide as well as oxidations and reductions, influence growth and development, and even lead to various diseases such as anemia; and iron deficiency anemia (IDA) will occur if the storage or intake of iron is insufficient. IDA refers to anemia which occurs when storage iron in the body available for producing hemoglobin has been depleted and erythropoiesis disorder develops. It is one of nutritional deficiency diseases with the highest incidence rate, and is common in children, pregnant and lactating women as well as patients with chronic diseases. According to a report from WHO (World Health Organization), about 10%-30% of the populations in the world suffer from iron deficiency at different levels, wherein the incidence rate is about 10% in male and >20% in female. An investigation shows that there are up to 38 million people suffering from anemia at different levels in China.

Nowadays, the prevention and treatment of iron deficiency anemia is mainly effected by iron supplementing agents. Conventional iron supplement agents include ferrous sulfate, ferrous chloride, ferrous gluconate, ferrous lactate, ferrous succinate, ferrous fumarate, etc. Although these iron supplement agents have high iron contents and good iron supplementing effects, they have a special rusty taste and are not suitable for long term consumption. In addition, they have low availability in human body and have significant adverse effects (various symptoms are prone to occur, e.g. bad smell, nausea, bloating, disorders of digestive organs, diarrhea, and constipation). Further, ferrous iron is unstable in gastrointestinal tract, and is prone to oxidation into ferric iron. Iron contained in heme of hemoglobin is in the form of ferrous iron, which will thus lead to low availability thereof in human body.

Ferroporphyrin (Porphyrin iron) belongs to natural substances, and is conventionally extracted from pig blood. It is a main component of erythrocytes and thus is also known as "heme". It is an iron porphyrin complex consisting of porphyrin and one molecular unit of ferrous iron. Porphyrin iron, known as a superior iron supplementing product, is free from being influenced by phosphoric acid, carbonic acid, tannic acid, oxalic acid, phytic acid, etc. and can be absorbed into blood directly by intestinal mucosa. Its bioavailability is lightly higher than conventional iron supplementing agents.

Although it has good iron supplementing effects, porphyrin iron has a special blood smell and consequently a poor taste, since it is extracted from pig blood. In addition, porphyrin iron is structurally unstable and prone to oxidation, and it also has an irritating effect on the digestive tract, e.g. stomach burning, nausea, etc., resulting in poor patient compliance to administration. Porphyrin iron is soluble in sodium hydroxide solution, hot alcohols or ammonia and slightly soluble in hot pyridine, but insoluble in water, diluted acids, ethers, chloroform, etc. Its absorption in gastrointestinal tract is limited by its relatively poor water solubility. According to a report by Zhao Di (Absorption Of $^{58}$Iron Originating From Hemin In Rat Using Extrinsically Label Method, *Chinese Journal of Clinical Pharmacology and Therapeutics*, 2012, 17(6): 639-643), the absolute oral bioavailability of porphyrin iron in rats is only 0.93%. On the other hand, porphyrin iron has an extremely low iron content in heme. As shown in the above structure, 6 rings of porphyrin are complexed with an iron atom, and thus during the absorption process, the ferrous ion can be released only after the 6 rings of porphyrin are destroyed. Therefore, in order to improve iron supplementing effects, the dosage of porphyrin iron should generally be increased. However, the increase in dosage will decrease the patient compliance to administration, leading to poor iron supplementing effects. Therefore, such disadvantages largely limit the development and application of porphyrin iron in foods and health products.

Most of current commercial porphyrin iron products are conventional porphyrin iron capsules without significant improvements in terms of the blood smell and irritations to digestive tract. In addition, oral porphyrin iron solution has been developed, to which casein phosphopeptides (CPP) for improving iron adsorption and Vitamins are added. This product not only fails to ameliorate the blood smell and digestive tract irritations or improve bioavailability of porphyrin iron, but also limits the application thereof, since CPP induces allergic responses in patients allergic to milk or seafoods due to the allergenicity of CPP.

Many patents and literatures relating to porphyrin iron have been disclosed and published, most of them focus on the extraction and preparation thereof, but few focus on ameliorating its blood smell or reducing its digestive tract irritations.

CN101254207A discloses a liposome preparation comprising porphyrin iron and/or inorganic iron, and preparation process thereof, wherein a liposome comprising porphyrin iron and/or inorganic iron, cholesterol and lecithin is prepared by utilizing a rotary thin film-ultrasonic process. The liposome preparation improves stability and bioavailability of porphyrin iron. However, the porphyrin iron liposome prepared by the process has an encapsulation rate of only 30-36%, and the lecithin in the preparation is prone to oxidation and is of high cost. In addition, the liposome per se has poor physical stability, which is unfavorable for storage and transportation and makes industrial production thereof difficult.

CN102726738A discloses an oil suspension type soft capsule with iron supplementing function, comprising iron materials (porphyrin iron/ferrous fumarate), Vitamin C, casein phosphopeptides, soybean oil, folic acid, beeswax, and gelatin capsule shells. Although the soft capsule can mask some of the blood smell and the Vitamin C and casein phosphopeptides added can improve the adsorption of iron in human body, Vitamin C per se is unstable and is prone to oxidation. Furthermore, there is a risk that CPP may induce allergies in patients allergic to milk or seafoods. Also, the soft capsule per se has a significant stability problem, i.e., the component of the capsule shell, gelatin, is prone to aging due to crosslinking reaction, resulting in a change in dissolubility of the capsule shell and thereby influencing the disintegration rate of the soft capsule. Furthermore, propylene glycol and sorbitol used in the capsule shell are prone to oxidation during storage, forming some low molecular weight aldehydes, thereby accelerating the crosslinking reaction of gelatin and in turn delaying the disintegration of the soft capsule.

Therefore, there is still a need for a porphyrin iron preparation which can not only overcome the disadvantages of porphyrin iron per se but also incorporate some stable, low cost and non-allergic adjuvants. In the meantime, it is desired to obtain a porphyrin iron composition with ameliorated digestive tract irritations and improved mouthfeel, bioavailability and/or stability by a simple and easy-operable formulation process.

SUMMARY OF THE INVENTION

In one aspect, the present invention provides a porphyrin iron solid dispersion, comprising porphyrin iron and a carrier material, wherein said carrier material is selected from one or more of polymers comprising vinylpyrrolidone units, or mixtures thereof; polymers comprising ethylene glycol units; and celluloses or cellulose esters.

In an embodiment of the present invention, porphyrin iron is dispersed in said carrier material at molecular level.

In another embodiment of the present invention, said polymers comprising vinylpyrrolidone units, or mixtures thereof are selected from one or more of polyvinylpyrrolidone, a mixture of polyvinylpyrrolidone and polyvinyl acetate, and a copolymer of vinylpyrrolidone and vinyl acetate.

In a further embodiment of the present invention, said polymers comprising vinylpyrrolidone units, or mixtures thereof have a K value of about 10-95, preferably 25-70. Said K value, also referred to as Fikentscher K value, is conventionally used in the art and is a measure of molecular weights of polymers comprising vinylpyrrolidone units, or mixtures thereof. It can be determined using a 1 wt. % aqueous solution according to a method as described in H. Fikentscher, Cellulose-Chemie, 1932, 13:58-64/71-74.

In a further embodiment of the present invention, the weight ratio of polyvinylpyrrolidone and polyvinyl acetate in said mixture of polyvinylpyrrolidone and polyvinyl acetate is about 1:9 to about 9:1, preferably about 2:8 to about 8:2.

In a further embodiment of the present invention, the weight ratio of vinylpyrrolidone units and vinyl acetate in said copolymer of vinylpyrrolidone and vinyl acetate is about 1:9 to about 9:1, preferably about 4:6 to about 6:4.

In a further embodiment of the present invention, said polymers comprising ethylene glycol units are copolymers of polyethylene glycol/vinyl caprolactam/vinyl acetate.

In a further embodiment of the present invention, said celluloses or cellulose esters are selected from one or more of methyl cellulose, hydroxymethyl cellulose, hydroxyethyl cellulose, hydroxypropyl cellulose, hydroxyethyl methyl cellulose and hydroxypropylmethyl cellulose, carboxymethyl cellulose, sodium carboxymethyl cellulose, carboxymethyl ethyl cellulose, hydroxypropylmethyl cellulose acetate succinate, hydroxypropylmethyl cellulose phthalate, and cellulose acetate phthalate, preferably hydroxypropylmethyl cellulose acetate succinate.

In a further embodiment of the present invention, in said hydroxypropylmethyl cellulose acetate succinate, the content of the acetate group is about 8 wt. % to about 12 wt. %, and the content of the succinate group is about 6 wt. % to about 15 wt. %, based on the weight of said hydroxypropylmethyl cellulose acetate succinate.

In a further embodiment of the present invention, the weight ratio of porphyrin iron to said carrier material in said porphyrin iron solid dispersion is about 1:1 to about 1:10, preferably about 1:1 to about 1:4, and more preferably about 1:1 to about 1:3.

In a further embodiment of the present invention, the porphyrin iron solid dispersion further comprises a pharmaceutically acceptable pharmaceutical adjuvant selected from one or more of surfactants, diluents, disintegrants, binders, and lubricants.

In another aspect, the present invention provides a process of preparing said porphyrin iron solid dispersion, including:
either feeding a homogenously mixed mixture of porphyrin iron and a carrier material at a weight ratio of 1:1 to 1:10, preferably 1:1 to 1:4, more preferably 1:1 to 1:3, and an optional pharmaceutically acceptable pharmaceutical adjuvant, or simply feeding porphyrin iron and a carrier material at said weight ratio and an optional pharmaceutically acceptable pharmaceutical adjuvant, into a hot melt extruder preheated to about 120° C. to about 180° C.; and
cooling, pulverizing, and sieving the extruded mixture, to obtain the porphyrin iron solid dispersion.

In another aspect, the present invention provides a pharmaceutical composition comprising said porphyrin iron solid dispersion, wherein the pharmaceutical composition is in the form of powders, granules, pills, capsules, or tablets.

In an embodiment of the present invention, said pharmaceutical composition further comprises a pharmaceutically acceptable pharmaceutical adjuvant selected from one or more of a surfactant, a diluent, a disintegrant, a binder, and a lubricant.

DETAILED DESCRIPTION OF THE INVENTION

Unless defined otherwise, the technical and scientific terms used herein have the same meaning as commonly understood by one skilled in the art to which this invention belongs. In case of discrepancy, the definitions provided in this application shall prevail.

When a certain quantity or concentration, or other values or parameters are represented in the form of ranges, preferred ranges, or preferred upper limit values or preferred lower limit values, it should be understood that this equals to that any ranges defined by combining any upper limits of the ranges or preferred values and any lower limits of the ranges or preferred values have been specifically suggested, regardless whether said ranges have been specifically disclosed. Unless indicated otherwise, a numerical range as listed herein is intended to include endpoints of the range and any integers and fractions within the range.

It should be understood that the term "about", when describing a value, or an endpoint of a range, is intended to include the specific value or related endpoint.

Unless indicated otherwise, all percentages, parts, and ratios as used herein are given by weight.

The present invention will be described in details below.

The present invention provides a porphyrin iron solid dispersion. As compared to prior art, the solid dispersion according to the present invention in which porphyrin iron is dispersed at molecular level, has advantages such as improved mouthfeel, low digestive tract irritation, high bioavailability, and high stability. Furthermore, the solid dispersion can be prepared by employing a hot melt extrusion process according to the present invention which is simple and easy-operable. Specifically, it has been found that a carrier material and porphyrin iron at a certain ratio can be prepared into a solid dispersion in which porphyrin iron is dispersed at molecular level after treatment with the hot melt extrusion process according to the present invention. Unexpectedly, it is found that the solid dispersion in which porphyrin iron is dispersed at molecular level can mask the blood smell of porphyrin iron, improve the mouthfeel of porphyrin iron significantly, reduce the irritations to digestive tract, such as symptoms e.g. stomach burning and nausea, induced by porphyrin iron, while significantly improving the solubility, in vitro dissolution rate and bioavailability of porphyrin iron. In addition, the hot melt extrusion process can also increase the chemical stability of porphyrin iron, and the process is simple and fairly good at repeatability.

The term "being dispersed at molecular level" in the present invention has a common meaning known by a person skilled in the art. Specifically, it means that porphyrin iron is dispersed in said carrier material at molecular level, forming a single-phase solid dispersion or solid solution. The Tg value of the resultant porphyrin iron solid dispersion is different from that of the carrier material.

The present invention provides a solid dispersion comprising porphyrin iron and a carrier material. Carrier materials suitable for the present invention include, but are not limited to, one or more of polymers comprising vinylpyrrolidone units, or mixtures thereof; polymers comprising ethylene glycol units; and celluloses or cellulose esters.

Said polymers comprising vinylpyrrolidone units, or mixtures thereof, suitable as the carrier, can be selected from one or more of polyvinylpyrrolidone, a mixture of polyvinylpyrrolidone and polyvinyl acetate, and a copolymer of vinylpyrrolidone and vinyl acetate.

Polyvinylpyrrolidone, also referred to as povidone, can be prepared, e.g., by free radical polymerization of vinylpyrrolidone in water or 2-propanol. Polyvinylpyrrolidone has a K value of about 10 to about 95, wherein the K value has the definition as described above. Polyvinylpyrrolidone suitable for the present invention can be purchased as, for example, Plasdone®K12, Plasdone®K17, Plasdone®K25, Plasdone®K29/32, Plasdone®K90 or Plasdone®K90D from International Specialty Products, or Kollidon®12PF, Kollidon®17PF, Kollidon®25, Kollidon®30, or Kollidon®90F from BASF, but is not limited thereto.

The weight ratio of polyvinylpyrrolidone to polyvinyl acetate in the mixture of polyvinylpyrrolidone and polyvinyl acetate, suitable as the carrier in the present invention, is about 1:9 to about 9:1, more preferably about 2:8 to about 8:2. Said mixture has a K value of about 50 to about 70. Said mixture of polyvinylpyrrolidone and polyvinyl acetate can be prepared, e.g., by physically mixing polyvinylpyrrolidone and polyvinyl acetate at the above mentioned ratio by spray drying. Said mixture of polyvinylpyrrolidone and polyvinyl acetate can also be, e.g., a mixture of polyvinylpyrrolidone and polyvinyl acetate at a weight ratio of 1:9 to 4:6, as disclosed in CN1227002C. The mixture of polyvinylpyrrolidone and polyvinyl acetate that can be used in the present invention can also be, e.g. the commercial product Kollidon®SR from BASF, which is a spray dried physical mixture of polyvinylpyrrolidone and polyvinyl acetate at a weight ratio of 2:8. In a preferred embodiment of the present invention, said carrier is Kollidon®SR.

The copolymer of vinylpyrrolidone and vinyl acetate, suitable as the carrier in the present invention, can be prepared, e.g., by carrying out free radical polymerization of N-vinylpyrrolidone and vinyl acetate in 2-propanol. Said copolymer of vinylpyrrolidone and vinyl acetate can also be a copolymer of vinylpyrrolidone and vinyl acetate at a weight ratio of 15:85-40:60, as disclosed in U.S. Pat. No. 5,426,163A. The weight ratio of vinylpyrrolidone and vinyl acetate in the copolymer suitable as the carrier in the present invention, is about 1:9 to about 9:1, preferably about 4:6 to about 6:4, and the copolymer has a K value of about 25 to about 70. The copolymer of vinylpyrrolidone and vinyl acetate that can be used in the present invention can also be, e.g. commercial product Kollidon®VA 64 from BASF and commercial product Plasdone®5630 from International Specialty Products (both are copolymers of vinylpyrrolidone and vinyl acetate at a weight ratio of 6:4), but is not limited thereto. In a preferred embodiment of the present invention, said carrier is Kollidon®VA 64.

The polymer comprising ethylene glycol units, suitable as the carrier in the present invention, can be, e.g., a copolymer of polyethylene glycol/vinyl caprolactam/vinyl acetate which can be, e.g., the commercial product Soluplus® from BASF. In a preferred embodiment of the present invention, said carrier is Soluplus®.

Celluloses suitable as the carrier in the present invention can be, e.g., methyl cellulose (MC), hydroxymethyl cellulose (HMC), hydroxylethyl cellulose (HEC), hydroxypropyl cellulose (HPC), hydroxyethyl methyl cellulose (HEMC) and hydroxypropylmethyl cellulose (HPMC), carboxymethyl cellulose (CMC), sodium carboxymethyl cellulose (CMC-Na), carboxymethyl ethyl cellulose (CMEC). Cellulose esters suitable as the carrier in the present invention can be, e.g., hydroxypropylmethyl cellulose acetate succinate (HPMCAS), hydroxypropylmethyl cellulose phthalate (HP-MCP), and cellulose acetate phthalate (CAP). In a preferred embodiment of the present invention, said carrier material is hydroxypropylmethyl cellulose acetate succinate, wherein the content of the acetate group is about 8 wt. % to about 12 wt. %, and the content of the succinate group is about 6 wt. % to about 15 wt. %, based on the weight of said hydroxypropylmethyl cellulose acetate succinate; and said hydroxypropylmethyl cellulose acetate succinate can be, e.g., commercial products AQOAT AS-L, AS-M and AS-H from Shin-Etsu. In a preferred embodiment of the present invention, said carrier is AQOAT AS-M.

In addition to the aforesaid carrier materials, polymethacrylic acids and salts thereof, methacrylate copolymers, aminoalkyl methacrylate copolymers; polyvinyl alcohol (PVA) and other materials, combinations thereof, and their combinations with the aforesaid materials can also be used as the carrier material according to the present invention.

The ratio of porphyrin iron, as the active ingredient, to the carrier material in the present invention is not specifically limited, and can be adjusted according to actual demands. Typically, the weight ratio of porphyrin iron to said carrier material is about 1:1 to about 1:10, preferably about 1:1 to about 1:4, and most preferably about 1:1 to about 1:3.

In another aspect, the present invention also provides a process of preparing the porphyrin iron solid dispersion according to the present invention, which includes, but is not limited to, hot extrusion process and spray drying process. For example, the hot extrusion process includes the following particular steps:

either feeding a homogenously mixed mixture of porphyrin iron and the carrier material at the above-mentioned weight ratio, and an optional pharmaceutically acceptable pharmaceutical adjuvant, or simply feeding porphyrin iron and the carrier material at the above-mentioned weight ratio and an optional pharmaceutically acceptable pharmaceutical adjuvant, into a hot melt extruder preheated to about 120° C. to about 180° C.; and cooling, pulverizing, and sieving the extruded mixture, to obtain the porphyrin iron solid dispersion.

The way to carry out the cooling described in the preparation process according to the present invention is not specifically limited, and it can include air cooling, water cooling, mechanical cooling, etc.

The type of the extruder suitable for the present invention is not specifically limited. It includes, but is not limited to, a single-screw or twin-screw hot melt extruder. In an embodiment of the present invention, the extruder for preparing the porphyrin iron solid dispersion according to the present invention is a twin-screw extruder. In that case, the rotation mode of the screw is not specifically limited, and it can include, but is not limited to, co-rotating twin screws, counter-rotating twin screws, and conical twin-screw rotating modes. In an embodiment of the present invention, the extruder for preparing the porphyrin iron solid dispersion according to the present invention is a co-rotating twin-screw extruder.

The melting temperature of the hot melt extruder is set to about 120° C. to about 180° C., and the rotation speed is set to about 50 to about 500 rpm. The length to diameter ratio (L/D) of the screw can be selected from about 15 to about 40. If the melting temperature is too low, the L/D is too low, or the rotation speed of the screw is too slow, then insufficient heat energy or mechanic energy will be provided during the hot melting process, and thus porphyrin iron (or the carrier material) will not achieve a melting state, or porphyrin iron will not dissolve in the molten carrier material. In that case, although being well mixed, porphyrin iron and the carrier material cannot form a single-phase solid dispersion which is dispersed at molecular level (solid solution). If the melting temperature is too high, the L/D is too high, or the rotation speed of the screw is too fast, then excess heat energy or mechanic energy will be provided during the hot melting process. In that case, even though a single-phase solid dispersion in which porphyrin iron is dispersed at molecular level (solid solution) is formed, unnecessary degradation of porphyrin iron and/or the carrier material will be caused.

Furthermore, the present invention also provides a pharmaceutical composition comprising the porphyrin iron solid dispersion. In an embodiment of the present invention, said pharmaceutical composition is in the form of powders, granules, pills, capsules, or tablets.

The porphyrin iron solid dispersion according to the present invention can also comprise a pharmaceutically acceptable pharmaceutical adjuvant. Moreover, the pharmaceutical composition according to the present invention can further be combined with a pharmaceutically acceptable pharmaceutical adjuvant according to actual demands, to form various solid dosage forms.

Said pharmaceutically acceptable pharmaceutical adjuvant includes, but is not limited to, one or more of surfactants, diluents, disintegrants, binders, and lubricants. Said surfactants are, e.g., polyethylene oxide-polypropylene oxide copolymers, such as poloxamer; and copolymers of polyethylene glycols, such as the Vitamin E polyethylene glycol 1000 succinate product from BASF, Kolliphor®TPGS. In a preferred embodiment of the present invention, said porphyrin iron solid dispersion comprises, as the surfactant, Vitamin E polyethylene glycol 1000 succinate. Said diluents can be one or more of microcrystalline cellulose, starch, pregelatinized starch, lactose, mannitol, and calcium hydrogen phosphate. Said disintegrants can be one or more of a low-substituted cellulose, croscarmellose sodium, sodium carboxymethyl starch, crosslinked polyvinylpyrrolidone. Said binders can be one or more of sodium carboxymethyl cellulose, hydroxypropyl cellulose, methyl cellulose, ethyl cellulose or hydroxypropylmethyl cellulose. Said lubricants can be one or more of magnesium stearate, talc powder, micronized silica gel, stearic acid, and hydrogenated vegetable oils.

DESCRIPTION OF THE DRAWINGS

The above and other objects and features of the present invention will be apparent with reference to the following figures.

FIG. 4: Profiles for dissolution of the porphyrin iron-Kollidon®VA 64 solid dispersions of various formulae under simulated in vivo conditions, wherein

EXAMPLES

Examples are provided below in order to describe the present invention in more details. The following examples are for the purpose of illustration only, and are not intended in any way to limit the present invention. A person skilled in the art will readily be aware of various non-critical parameters, and is able to modify or change these parameters to obtain substantially the same results.

Preparation of Porphyrin Iron-Kollidon®VA 64 Solid Dispersions

Example 1-1. Preparation of Porphyrin Iron-Kollidon®VA 64 Solid Dispersions

The particular weight ratios in various solid dispersion formulae are shown in Table 1-1.

TABLE 1-1

Specific composition of various solid dispersion formulae

| Names of raw materials and adjuvants | Amounts of raw materials and adjuvants (g) | | | |
|---|---|---|---|---|
| | Formula 1-1 | Formula 1-2 | Formula 1-3 | Formula 1-4 |
| porphyrin iron | 35 | 50 | 50 | 20 |
| Kollidon ® VA 64 | 35 | 150 | 150 | 200 |
| Kolliphor ® TPGS | None | None | 20 | None |

Preparation process: Porphyrin iron and the carrier materials in the amounts shown in the formulae in Table 1-1 were added to a mixer separately and mixed homogenously. Alternatively, porphyrin iron and the carrier materials in the amounts shown in the formulae in Table 1-1 were fed into the loading hopper of a co-rotating twin screw extruder (Omicron 12, Steer Engineering Private Limited, India). The melting temperature in the co-rotating twin screw extruder was controlled at between about 120° C. and about 180° C., and the rotation speed of the screw was about 50 to about 500 rpm. The extruded mixtures were cooled, pulverized, and sieved, to obtain the solid dispersion.

Evaluation on the Physical and Chemical Properties of the Porphyrin Iron-Kollidon®VA 64 Solid Dispersions Test Example 1-2. Determination of Glass Transition Temperature (Tg) of the Solid Dispersions >3 mg of the active pharmaceutical ingredient (API) porphyrin iron, extruded blank material prepared from Kollidon®VA 64, and materials prepared according to the formulae in Table 1-1 were precisely weighted separately, and were subjected to differential scanning calorimetry analysis (mDSC analysis, TA Q2000 Differential Scanning calorimeter). The test results showed that no melting point or Tg value was determined in the scanning of the API porphyrin iron (crystalline type) in the temperature range of 40-180° C., since crystalline porphyrin iron was completely decomposed before the melting point was reached. The blank Kollidon®VA 64 solid dispersion had a Tg value of 98.73° C. and Formula 1-2 had a Tg value of 101.3° C. The Tg value of Formula 1-2 showed a significant deviation as compared to the blank solid dispersion and also was different from the Tg value of porphyrin iron, indicating that porphyrin iron was in the state of being dispersed at molecular level in the dispersion, it formed a solid dispersion or a solid solution with the carrier adjuvant.

Test Example 1-3. Determination of the Content of Porphyrin Iron in the Solid Dispersions Sample preparation: an appropriate amount of the solid dispersion of each formula was weighted, and was dissolved in 0.1N aqueous NaOH solution, to prepare a test sample with a porphyrin iron concentration of about 50 μg/ml. Analysis was conducted by an HPLC method. The method for determining the content was as follows, and the results were shown in Table 1-2.

| | |
|---|---|
| Chromatography column | C18 column (3 μm, 3.0 × 50 mm) |
| Mobile phase | 0.2% phosphoric acid/methanol = 25:75 |
| Flow rate | 1 ml/min |
| Sample disk | Room temperature |
| Wavelength | 401 nm |
| Sample injection | 10 μl |
| Analysis period for single sample injection | About 2 min |

TABLE 1-2

Content determination results for each solid dispersion formula

| | Formula | | | |
|---|---|---|---|---|
| | Formula 1-1 | Formula 1-2 | Formula 1-3 | Formula 1-4 |
| Labelled amount (%) | 93.3 | 95.7 | 97.1 | 96.5 |

As can be seen from Table 1-2, the labelled amounts of the drug for all formulae were >93%, indicating that the hot melt extrusion process had little influence on the stability of the drug. The relatively lower labelled amounts of the drug were due to about 3%-6% of water contained in the solid dispersions.

Test Example 1-4. Determination of the Apparent Solubility of the Solid Dispersions Sample preparation: Excess amounts of porphyrin iron solid dispersions of various formulae and physical mixtures of porphyrin iron and carrier materials (prepared by weighting the active pharmaceutical ingredient and the carrier adjuvants in the amounts shown in the formulae and simply mixing them) were weighted separately, and placed in appropriate containers, a phosphate buffer solution having a pH of 6.8 and a volume of about ⅔ of the volume of the container was added, and then it was placed in a shaking table at 37° C. and was shaken for 24 h. The resultant solution was filtered through a 0.45 μm filter membrane, and then the filtrate was collected, further diluted with an appropriate amount of 0.1N NaOH, and analyzed by HPLC after vortex mixing. The analysis method was the same as the method for the content determination for the solid dispersions in Example 1-3. The determination results were shown in Table 1-3.

TABLE 1-3

Determination results of porphyrin iron solubility for each solid dispersion formula

| | API | Formula 1-1 A[1] | Formula 1-1 B[2] | Formula 1-2 A | Formula 1-2 B | Formula 1-3 B | Formula 1-4 A | Formula 1-4 B |
|---|---|---|---|---|---|---|---|---|
| Solubility (μg/ml) | <0.2 | 2.5 | 239.9 | 1.2 | 606.3 | 126.4 | 1.1 | 360.6 |
| Solubility ratio (solid dispersion/API) | —[3] | | >1200 | | >3032 | >632 | | >1803 |
| Solubility ratio (solid dispersion/ physical mixture) | — | | 96 | | 505 | 79 | | 328 |

[1]"A" represents a physical mixture (not a solid dispersion of the present invention) with the same composition as sample B.
[2]"B" represents a solid dispersion of the present invention.
[3]"—" means that there is no determined value.

Figure 1:
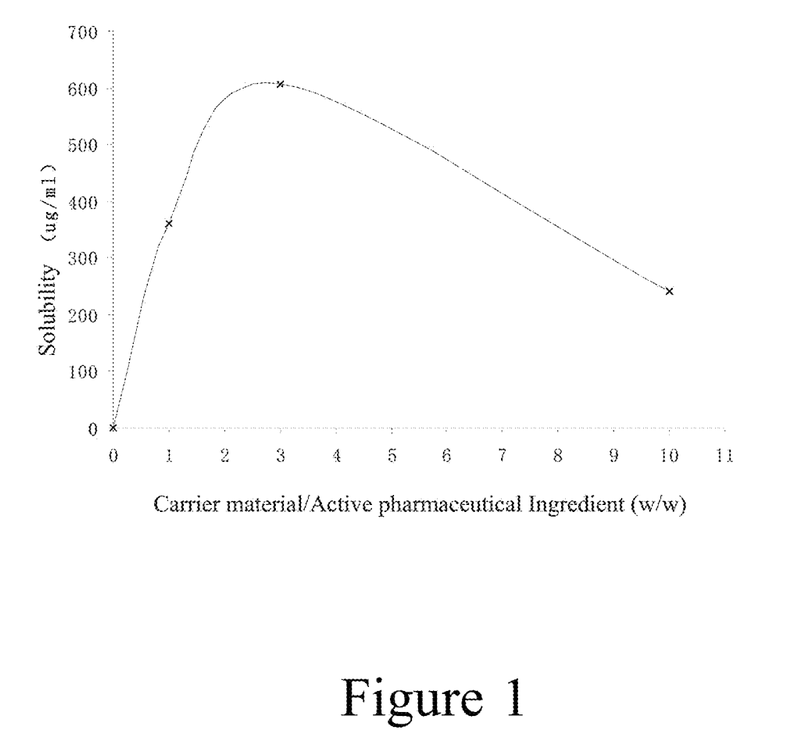
FIG. 1: Influences of the weight ratio of carrier material/active pharmaceutical ingredient in the porphyrin iron-Kollidon®VA 64 solid dispersions of various formulae on the solubility of porphyrin iron.
Figure 2:
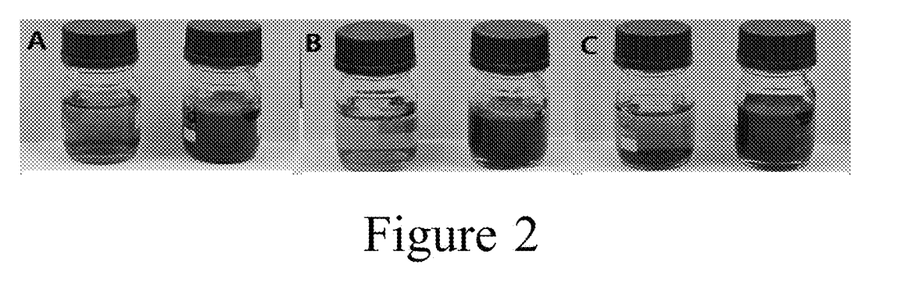
FIG. 2: Photographs for the solubility of the porphyrin iron-Kollidon®VA 64 solid dispersions of various formulae, wherein A corresponds to Formula 1-1, B corresponds to Formula 1-2, and C corresponds to Formula 1-4.

As can be seen from the solubility determination results in Table 1-3, all solid dispersions of various formulae prepared by a hot melt extrusion process had significant solubilizing effects on porphyrin iron, indicating that Kollidon®VA 64 had fairly good solubilizing effects on porphyrin iron. As can be seen from the results obtained from a single-variable design of experiment (DOE), there is a certain relationship between the weight ratio of the carrier (Kollidon®VA 64) to the API porphyrin iron in the solid dispersions and the solubility of porphyrin iron in the solid dispersions, as shown in FIG. 1. Especially, the solubility of porphyrin iron in the solid dispersions reached its maximum when the weight ratio of the carrier to the API porphyrin iron was 3:1. In FIG. 2, when being dispersed in the buffer at pH 6.8 for 3 min, all the prepared solid dispersions of various formulae had colors significantly deeper than those of the physical mixtures, indicating that the solid dispersions, which were prepared with the carriers and in which porphyrin iron was in the state of being dispersed at molecular level, could largely increase the solubility of porphyrin iron.

Test Example 1-5. In Vitro Dissolution Tests for the Solid Dispersions

Conditions for the Dissolution Tests:

| Dissolution method | USP Method II (Paddle) |
|---|---|
| Dissolution medium | pH 1.2/pH 6.8 |
| Medium volume | 900 ml |
| Rotation speed | 100 rpm |
| Temperature | 37.5° C. |
| Tested dosage | 50 mg (porphyrin iron)/cup |

Analysis method for sample dissolution: the same as that for the content determination for the solid dispersions in Example 1-3.

The in vitro dissolution results for the solid dispersions were shown in Table 1-4 and Table 1-5.

TABLE 1-4

Results of the dissolution tests for solid dispersions of various formulae in the dissolution medium at pH 1.2

| Test samples | Concentrations of dissolved API at various time points (μg/ml) | | | | | |
|---|---|---|---|---|---|---|
| | 5 min | 10 min | 15 min | 30 min | 45 min | 60 min |
| Physical mixture[1] | <0.2 | <0.2 | <0.2 | <0.2 | <0.2 | <0.2 |
| Formula 1-1 | 55.1 | 52.8 | 55.7 | 52.8 | 54.9 | 54.3 |
| Formula 1-2 | 52.2 | 54.0 | 52.6 | 54.3 | 54.0 | 53.9 |
| Formula 1-3 | 48.8 | 51.3 | 49.6 | 49.7 | 49.5 | 49.1 |
| Formula 1-4 | 45.4 | 46.8 | 49.0 | 49.8 | 47.2 | 49.0 |

[1]said physical mixture was prepared according to the specific composition of Formula 1-2.

TABLE 1-5

Results of the dissolution tests for the solid dispersions of various formulae in the dissolution medium at pH 6.8

| Test samples | Concentrations of dissolved API at various time points (μg/ml) | | | | | |
|---|---|---|---|---|---|---|
| | 15 min | 30 min | 45 min | 60 min | 120 min | 180 min |
| Physical mixture[1] | <0.2 | <0.2 | <0.2 | <0.2 | <0.2 | <0.2 |
| Formula 1-1 | 56.8 | 56.1 | 55.9 | 56.0 | 55.8 | 54.8 |
| Formula 1-2 | 54.2 | 54.9 | 53.6 | 53.8 | 53.8 | 54.5 |
| Formula 1-3 | 45.9 | 46.3 | 44.4 | 42.5 | 45.8 | 47.8 |
| Formula 1-4 | 55.1 | 55.4 | 55.2 | 54.3 | 54.9 | 54.2 |

[1]said physical mixture was prepared according to the specific composition of Formula 1-2.

Figure 3:
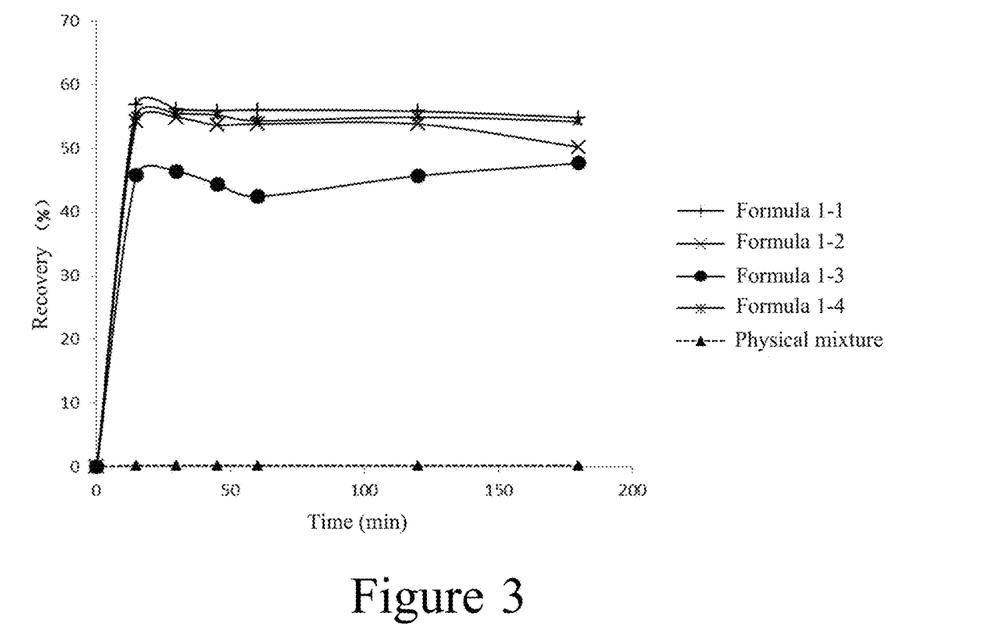
FIG. 3: Profiles for in vitro dissolution of the porphyrin iron-Kollidon®VA 64 solid dispersions of various formulae.
Figure 4A:
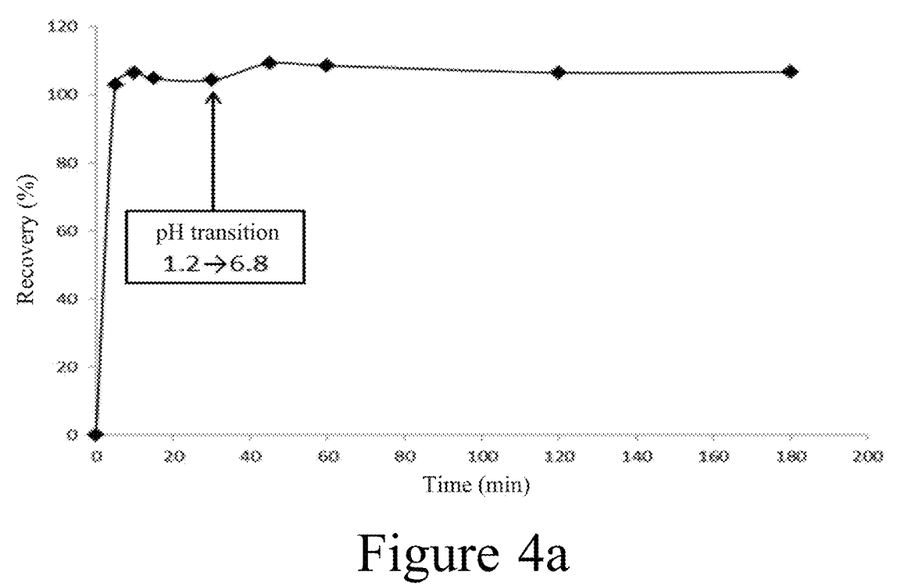
FIG. 4a is a profile for in vitro dissolution under simulated gastric fluid in the fasted conditions.
Figure 4B:
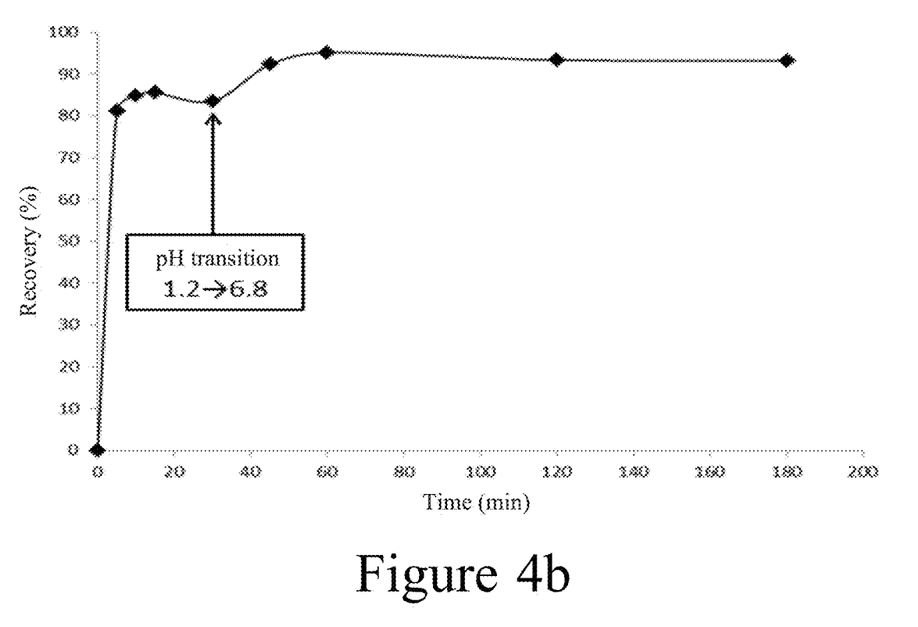
FIG. 4b is a profile for in vitro dissolution under simulated gastric fluid in the fed conditions.

As can be seen from Table 1-4 and Table 1-5, as compared to the physical mixture, solid dispersions of various formulae prepared by using Kollidon®VA 64 as the carrier material could largely increase the concentration of dissolved porphyrin iron and the dissolution rate of porphyrin iron at pH 1.2 and pH 6.8. FIG. 3 shows profiles for in vitro dissolution of the porphyrin iron-Kollidon®VA 64 solid dispersions of various formulae and the physical mixture of porphyrin iron-Kollidon®VA 64 in the medium at pH 6.8, wherein the concentration of the physical mixture at each time point was lower than that represented by the dotted line in the figure.

Test Example 1-6. Dissolution Tests Under Stimulated In Vivo Conditions

The pH of gastric fluid is about 1.2 and that of intestinal fluid is about 6.8 in human in the fasted conditions. The pH of gastric fluid might be still as low as 1.2 and that of intestinal fluid is about 5.0 due to the influences from foods. In this test example, Formula 1-2, having a maximal solubility, was selected for dissolution tests under stimulated in vivo conditions. The test conditions were shown below.

| | |
|---|---|
| Dissolution method | USP method II (Paddle) |
| Dissolution medium | A medium of pH 1.2→6.8: 800 ml of a dissolution medium of pH 1.2 was sampled over 30 min, and then 100 ml of a prepared buffer solution was immediately added so that the pH of the overall dissolution medium was 6.8. A medium of pH 1.2→5.0: 800 ml of a dissolution medium of pH 1.2 was sampled over 30 min, and then 100 ml of a prepared buffer solution was immediately added so that the pH of the overall dissolution medium was 5.0. |
| Rotation speed | 100 rpm |
| Temperature | 37.5° C. |
| Tested dosage | 60 mg (porphyrin iron)/cup |

Analysis method for sample dissolution: the same as that for the content determination for the solid dispersions in Example 1-3.

The in vitro dissolution results for the solid dispersions were shown in Table 1-6 and Table 1-7.

TABLE 1-6

Results of the dissolution test for Formula 1-2 during medium transition pH 1.2→6.8

| | Dissolution at various time points (%) | | | | | | | |
|---|---|---|---|---|---|---|---|---|
| | pH 1.2 | | | | pH 6.8 | | | |
| Test sample | 5 min | 10 min | 15 min | 30 min | 45 min | 60 min | 120 min | 180 min |
| Formula 1-2 | 103.0 | 106.5 | 104.7 | 104.3 | 109.3 | 108.6 | 106.5 | 106.7 |

TABLE 1-7

Results of the dissolution test for Formula 1-2 during medium transition pH 1.2→5.0

| | Dissolution at various time points (%) | | | | | | | |
|---|---|---|---|---|---|---|---|---|
| | pH 1.2 | | | | pH 5.0 | | | |
| Test sample | 5 min | 10 min | 15 min | 30 min | 45 min | 60 min | 120 min | 180 min |
| Formula 1-2 | 81.2 | 84.9 | 85.5 | 83.5 | 92.3 | 95.1 | 93.3 | 93.2 |

As can be seen from Table 1-6 and Table 1-7, the dissolution of Formula 1-2 under both stimulated in vivo fasted conditions (pH 1.2→6.8 medium transition) and fed conditions (pH 1.2→5.0 medium transition) were above 80%, indicating that the transition from gastric fluid to intestinal fluid of different pH had little influence on the dissolution of the solid dispersion of Formula 1-2.

Test Example 1-7. Stability Test for the Solid Dispersions

A certain amount of the API porphyrin iron and the solid dispersion of Formula 1-2 were placed in 30 mL brown glass vials, and the method of the sample stability test was the same as the method for the content determination for the solid dispersions in Example 1-3. The test results were shown in Table 1-8 and Table 1-9.

TABLE 1-8

Content determination results of the stability study for the porphyrin iron-Kollidon ®VA 64 solid dispersion (open)

| | | Test period | | | | |
|---|---|---|---|---|---|---|
| Samples | Test conditions | 0 day | 1 day | 3 days | 7 days | 35 days |
| API | 25° C. | 100.9% | 98.0% | 98.7% | 100.9% | 98.8% |
| Formula 1-2 | 60% RH | 100.5% | 97.6% | 97.9% | 98.6% | 97.8% |
| API | 40° C. | 100.9% | 99.0% | 99.8% | 100.8% | 100.6% |
| Formula 1-2 | 75% RH | 100.5% | 98.3% | 96.2% | 96.9% | 97.6% |

TABLE 1-9

Content determination results of the stability study for the porphyrin iron-Kollidon ®VA 64 solid dispersion (sealed)

| | | Test period | | | | | |
|---|---|---|---|---|---|---|---|
| Samples | Test conditions | 0 day | 1 day | 3 days | 7 days | 14 days | 35 days |
| API | 25° C. | 100.9% | 99.5% | 102.0% | 100.5% | 98.9% | 102.2% |
| Formula 1-2 | 60% RH | 100.5% | 98.8% | 101.6% | 99.6% | 97.6% | 100.8% |
| API | 40° C. | 100.9% | 99.6% | 102.7% | 100.8% | 99.2% | 102.7% |
| Formula 1-2 | 75% RH | 100.5% | 98.8% | 100.4% | 98.2% | 98.1% | 96.6% |

As can be seen from Table 1-8 and Table 1-9, for the API porphyrin iron and the porphyrin iron-Kollidon®VA 64 solid dispersion, after being placed at 25° C. 60% RH and 40° C. 75% RH for 35 days, the contents of porphyrin iron were within the confidence interval of 96%-104% of the analysis method established for the content determination for the solid dispersions in Example 1-3. The slightly lower labelled amounts of the drug were due to about 3% water contained in the solid dispersion. The test results indicated that porphyrin iron was very stable in the porphyrin iron-Kollidon®VA 64 solid dispersion.

Preparation of Porphyrin Iron-Soluplus® Solid Dispersions

Example 2-1. Preparation of Porphyrin Iron-Soluplus® Solid Dispersion

Formula: The specific composition of each solid dispersion formula was shown in Table 2-1.

TABLE 2-1

Specific composition of each solid dispersion formula

| Names of raw materials and adjuvants | Amounts of raw materials and adjuvants (g) | | |
|---|---|---|---|
| | Formula 2-1 | Formula 2-2 | Formula 2-3 |
| porphyrin iron | 35 | 30 | 20 |
| Soluplus ® | 35 | 90 | 200 |

Preparation process: Porphyrin iron and the carrier material in the amounts shown in the formulae in Table 2-1 were added to a mixer separately and mixed homogenously. Alternatively, porphyrin iron and the carrier material in the amounts shown in the formulae in Table 2-1 were fed into a loading hopper of a co-rotating twin screw extruder (Omicron 12, Steer Engineering Private Limited, India). The melting temperature in the screw extruder was controlled at about 120° C. to about 180° C., and the rotation speed of the screw was about 50 to about 500 rpm. The extruded mixtures were cooled, pulverized, and sieved, to obtain the solid dispersions.

Evaluation on the Physical And Chemical Properties of the Porphyrin Iron-Soluplus® Solid Dispersions Test Example 2-2. Determination of the Content of Porphyrin Iron in the Solid Dispersions Sample preparation: an appropriate amount of the solid dispersion of each formula was weighted and dissolved in 0.1N aqueous NaOH solution, to prepare a test sample with a porphyrin iron concentration of about 50 µg/ml. Analysis was conducted by a HPLC method. The analysis method for the content determination was the same as that for the content determination for the solid dispersions in Example 1-3. The results were shown in Table 2-2.

TABLE 2-2

Content determination results for each solid dispersion formula

| | Formula | | |
|---|---|---|---|
| | Formula 2-1 | Formula 2-2 | Formula 2-3 |
| Labelled amount (%) | 94.7 | 92.0 | 93.5 |

As can be seen from Table 2-2, the labelled amounts of the drug for all formulae after being extruded were above 90%, indicating that the hot melt extrusion process had little influence on the stability of the drug. The slightly lower labelled amounts of the drug were due to about 3%-6% of water contained in the solid dispersions.

Test Example 2-3. Determination of the Apparent Solubility of the Solid Dispersions Sample preparation: Excess amounts of the porphyrin iron solid dispersions of various formulae and physical mixtures of porphyrin iron and the carrier material (prepared by weighting the active pharmaceutical ingredient and the carrier adjuvant in the amounts shown in the formulae and simply mixing them) were weighted separately, and placed in appropriate containers, a phosphate buffer solution having a pH of 6.8 and a volume of about ⅔ of the volume of the container was added, and then it was placed in a shaking table at 37° C. and was shaken for 24 h. The resultant solution was filtered through a 0.45 µm filter membrane, and then the filtrate was collected, further diluted with an appropriate amount of 0.1N NaOH, and analyzed by HPLC after vortex mixing. The analysis method was the same as the method for the content determination for the solid dispersions in Example 1-3. The determination results were shown in Table 2-3.

TABLE 2-3

Solubility determination results for each solid dispersion formula

| | | Formula | | | | | |
|---|---|---|---|---|---|---|---|
| | | Formula 2-1 | | Formula 2-2 | | Formula 2-3 | |
| | API | A[1] | B[2] | A | B | A | B |
| Solubility (µg/ml) | <0.2 | <0.6 | 33.8 | 1.3 | 28.1 | <0.6 | 69.7 |
| Solubility ratio (solid dispersion/API) | | —[3] | >169 | | >140 | | >348 |
| Solubility ratio (solid dispersion/ physical mixture) | | — | >56 | | 22 | | >116 |

[1] "A" represents a physical mixture (not a solid dispersion of the present invention) with the same composition as sample B.
[2] "B" represents a solid dispersion of the present invention.
[3] "—" means that there is no determined value.

Figure 5:
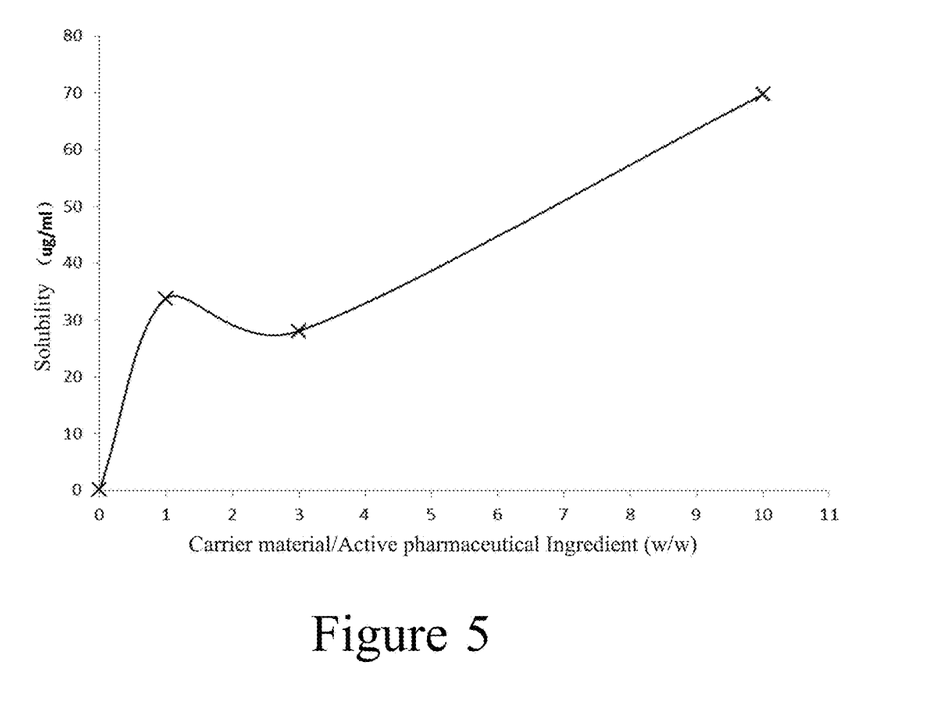
FIG. 5: Influences of the ratio of carrier material/active pharmaceutical ingredient in the porphyrin iron-Soluplus® solid dispersion of Formula 1-2 on the solubility of porphyrin iron.
Figure 6:
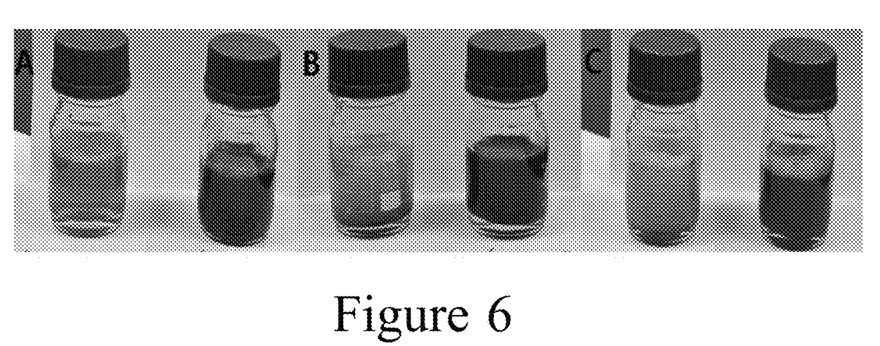
FIG. 6: Photographs for the solubility of the porphyrin iron-Soluplus® solid dispersions of various formulae, wherein A corresponds to Formula 2-1, B corresponds to Formula 2-2, and C corresponds to Formula 2-3.

As can be seen from the solubility determination results in Table 2-3 and FIG. 5, all Soluplus® solid dispersions of various formulae prepared by a hot melt extrusion process had significant solubilizing effects on porphyrin iron. As can be seen from the results obtained from the single-variable design of experiment (DOE), there is a certain relationship between the weight ratio of the carrier to porphyrin iron in the solid dispersions and the solubility of porphyrin iron in the solid dispersions. As shown in FIG. 5, the solubility of porphyrin iron in the solid dispersions was increased with the increase of the weight ratio of the carrier to porphyrin iron. Soluplus® had fairly good solubilizing effects on porphyrin iron. In FIG. 6, when being dispersed in the buffer at pH 6.8 for 3 min, all the prepared solid dispersions of various formulae had colors significantly deeper than those of the physical mixtures, indicating that the solid dispersions, which were prepared with Soluplus® and in which porphyrin iron was in the state of being dispersed at molecular level, could largely increase the solubility of porphyrin iron.

Test Example 2-4. In Vitro Dissolution Tests for the Solid Dispersions

The conditions for the dissolution tests were the same as the dissolution tests of the solid dispersions in Example 1-5.

The analysis method for sample dissolution was the same as that for the content determination for the solid dispersions in Example 1-3. The results were shown in Table 2-4 and Table 2-5.

TABLE 2-4

Results of the dissolution tests for the solid dispersions of various formulae in the dissolution medium at pH 1.2

| Test samples | Concentrations of dissolved API at various time points (μg/ml) | | | | | |
|---|---|---|---|---|---|---|
| | 5 min | 10 min | 15 min | 30 min | 45 min | 60 min |
| Formula 2-1 | 2.4 | 2.3 | 1.89 | 2.6 | 3.9 | 2.9 |
| Formula 2-2 | 6.6 | 12.2 | 6.8 | 5.2 | 6.6 | 3.4 |
| Formula 2-3 | 37.0 | 34.1 | 36.0 | 36.5 | 34.9 | 36.5 |

TABLE 2-5

Results of the dissolution tests for the solid dispersions of various formulae in the dissolution medium at pH 6.8

| Test samples | Concentrations of dissolved API at various time points (μg/ml) | | | | | |
|---|---|---|---|---|---|---|
| | 15 min | 30 min | 45 min | 60 min | 120 min | 180 min |
| Formula 2-1 | 1.8 | 2.7 | 3.0 | 2.5 | 3.4 | 2.8 |
| Formula 2-2 | 4.2 | 3.3 | 3.1 | 3.2 | 1.8 | 2.3 |
| Formula 2-3 | 1.9 | 2.3 | 1.9 | 2.2 | 2.2 | 2.2 |

As can be seen from Table 2-4 and Table 2-5, each formula containing Soluplus® can increase the concentration of dissolved porphyrin iron and the dissolution rate of porphyrin iron.

Preparation of Porphyrin Iron-HPMCAS Solid Dispersions

Example 3-1. Preparation of Porphyrin Iron-HPMCAS (AQOAT AS-M) Solid Dispersions Formula: The specific composition of each solid dispersion formula was shown in Table 3-1.

TABLE 3-1

Specific composition of each solid dispersion formula

| Names of raw materials and adjuvants | Amounts of raw materials and adjuvants (g) | | |
|---|---|---|---|
| | Formula 3-1 | Formula 3-2 | Formula 3-3 |
| porphyrin iron | 35 | 50 | 20 |
| HPMCAS | 35 | 150 | 200 |

Preparation process: Porphyrin iron and the carrier material in the amounts shown in the formulae in Table 3-1 were added to a mixer separately and mixed homogenously. Alternatively, porphyrin iron and the carrier material in the amounts shown in the formulae in Table 3-1 were fed into a loading hopper of a co-rotating twin screw extruder (Omicron 12, Steer Engineering Private Limited, India). The melting temperature in the screw extruder was controlled at about 120° C. to about 180° C., and the rotation speed of the screw was about 50 to about 500 rpm. The extruded mixtures were cooled, pulverized, and sieved, to obtain the solid dispersions.

Evaluation on the Physical and Chemical Properties of the Porphyrin Iron-HPMCAS Solid Dispersions Test Example 3-2. Determination of the Content of Porphyrin Iron in the Solid Dispersions Sample preparation: an appropriate amount of the solid dispersion of each formula was weighted, and dissolved in 0.1N aqueous NaOH solution, to prepare a test sample with a porphyrin iron concentration of about 50 μg/ml. Analysis was conducted by a HPLC method. The analysis method for the content determination was the same as that for the content determination for the solid dispersions in Example 1-3. The results were shown in Table 3-2.

TABLE 3-2

Content determination results for each solid dispersion formula

| | Formula | | |
|---|---|---|---|
| | Formula 3-1 | Formula 3-2 | Formula 3-3 |
| Labelled amount (%) | 95.6 | 85.5 | 91.7 |

As can be seen from Table 3-2, the labelled amounts of the drug for all formulae after being extruded were above 85%, indicating that the hot melt extrusion process had little influence on the stability of the drug. The slightly lower labelled amounts of the drug were due to about 3%-6% of water contained in the solid dispersions.

Test Example 3-3. Determination of the Apparent Solubility of the Solid Dispersions Sample preparation: Excess amounts of the porphyrin iron solid dispersions of various formulae and the physical mixture of porphyrin iron and the carrier material (prepared by weighting the active pharmaceutical ingredient and the carrier adjuvant in the amounts shown in the formulae and simply mixing them) were weighted separately, and placed in appropriate containers, a phosphate buffer solution having a pH of 6.8 and a volume of about ⅔ of the volume of the container was added, and then it was placed in a shaking table at 37° C. and was shaken for 24 h. The resultant solution was filtered through a 0.45 μm filter membrane, and then the filtrate was collected, further diluted with an appropriate amount of 0.1N NaOH, and analyzed by HPLC after vortex mixing. The analysis method was the same as the method for the content determination for the solid dispersions in Example 1-3. The determination results were shown in Table 3-3.

TABLE 3-3

Solubility determination results for each solid dispersion formula

|  |  | Formula | | | | | |
|---|---|---|---|---|---|---|---|
|  |  | Formula 3-1 | | Formula 3-2 | | Formula 3-3 | |
|  | API | A[1] | B[2] | A | B | A | B |
| Solubility (μg/ml) | <0.2 | <0.2 | 71.1 | <0.2 | 66.0 | <0.2 | 54.0 |
| Solubility ratio (solid dispersion/API) | —[3] |  | >355 |  | >330 |  | >270 |
| Solubility ratio (solid dispersion/ physical mixture) | — |  | >355 |  | >330 |  | >270 |

[1] "A" represents a physical mixture (not a solid dispersion of the present invention) with the same composition as sample B.
[2] "B" represents a solid dispersion of the present invention.
[3] "—" means that there is no determined value.

Figure 7:
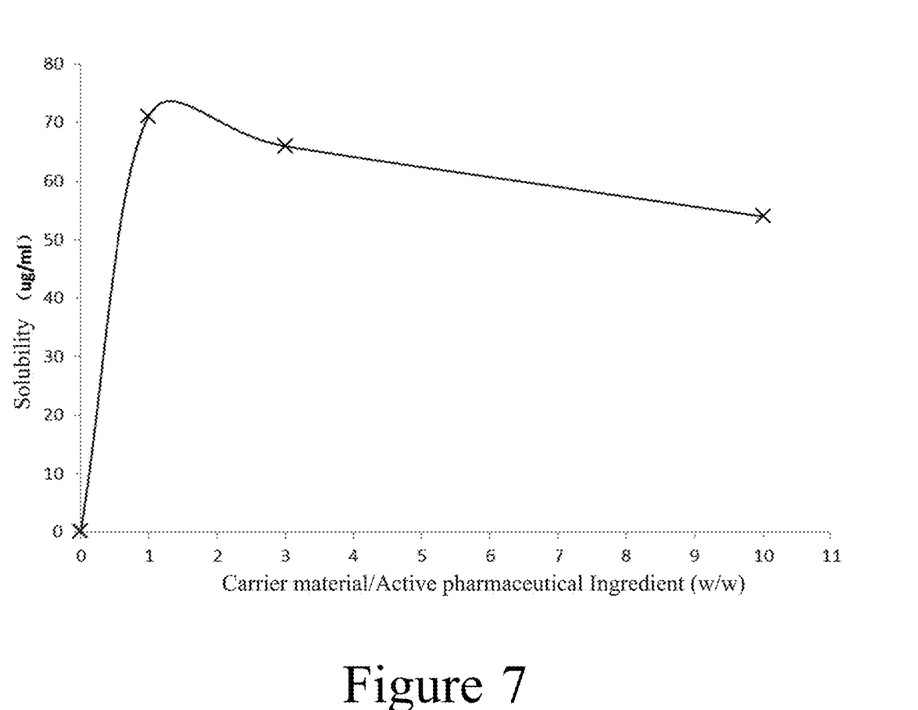
FIG. 7: Influences of the ratio of carrier material/active pharmaceutical ingredient in porphyrin iron-HPMCAS solid dispersions on the solubility of porphyrin iron.
Figure 8:
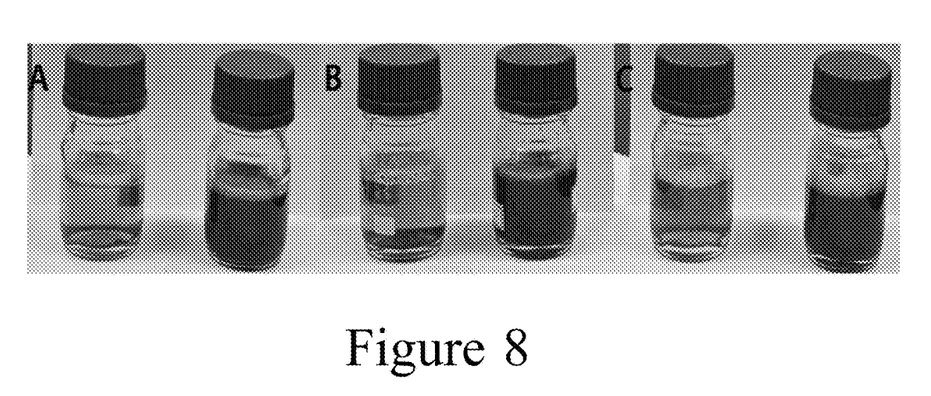
FIG. 8: Photographs for the solubility of porphyrin iron-HPMCAS solid dispersions of various formulae, wherein A corresponds to Formula 3-1, B corresponds to Formula 3-2, and C corresponds to Formula 3-3.

As can be seen from the solubility determination results in Table 3-3 and FIG. 7, all HPMCAS solid dispersions of various formulae prepared by the hot melt extrusion process had significant solubilizing effects on porphyrin iron. As can be seen from the results obtained from the single-variable design of experiment (DOE), there is a certain relationship between the weight ratio of the carrier to porphyrin iron in the solid dispersions and the solubility of porphyrin iron in the solid dispersions. As shown in FIG. 7, the solubility of porphyrin iron in the solid dispersions was slightly decreased with the increase of the weight ratio of the carrier to porphyrin iron. In FIG. 8, when being dispersed in the buffer at pH 6.8 for 3 min, all the prepared solid dispersions of various formulae had colors significantly deeper than those of the physical mixtures, indicating that the solid dispersion technique could largely increase the solubility of porphyrin iron.

Test Example 3-4. In Vitro Dissolution Tests of the Solid Dispersions

The conditions for the dissolution tests were the same as the dissolution tests of the solid dispersions in Example 1-5. The analysis method for sample dissolution was the same as that for the content determination for the solid dispersions in Example 1-3. The results were shown in Table 3-4 and Table 3-5.

TABLE 3-4

Results of the dissolution tests for the solid dispersions of various formulae in the dissolution medium at pH 1.2

|  | Concentrations of dissolved API at various time points (μg/ml) | | | | | |
|---|---|---|---|---|---|---|
| Test samples | 5 min | 10 min | 15 min | 30 min | 45 min | 60 min |
| Formula 3-1 | <0.3 | <0.3 | <0.3 | <0.3 | <0.3 | <0.3 |
| Formula 3-2 | 1.0 | 1.1 | 1.1 | 1.1 | 1.2 | 1.2 |
| Formula 3-3 | <0.3 | <0.3 | <0.3 | <0.3 | <0.3 | <0.3 |

TABLE 3-5

Results of the dissolution tests for the solid dispersions of various formulae in the dissolution medium at pH 6.8

|  | Concentrations of dissolved API at various time points (μg/ml) | | | | | |
|---|---|---|---|---|---|---|
| Test samples | 15 min | 30 min | 45 min | 60 min | 120 min | 180 min |
| Formula 3-1 | 44.7 | 44.3 | 42.4 | 43.6 | 43.3 | 44.4 |
| Formula 3-2 | 44.7 | 49.5 | 50.7 | 50.6 | 25.8 | 26.1 |
| Formula 3-3 | 47.9 | 49.2 | 48.1 | 47.3 | 48.5 | 49.0 |

As can be seen from Table 3-4 and Table 3-5, the HPMCAS solid dispersion of each formula can increase the concentration of dissolved porphyrin iron and the dissolution rate of porphyrin iron in the medium at pH 6.8. The dissolved amounts in the medium at pH 1.2 were very few, since HPMCAS was an enteric material.

Example 4. Clinical Tests on the Mouthfeel and Gastrointestinal Tract Irritation of Porphyrin Iron Solid Dispersions In order to evaluate the mouthfeel and gastrointestinal tract irritation of porphyrin iron solid dispersions, 6 healthy volunteers were enrolled in tests on the mouthfeel and gastrointestinal tract irritation for the samples such as Formula 1-1, Formula 1-2, Formula 1-4, Formula 2-2, Formula 3-2 and the API of porphyrin iron. The test results were summarized in Table 4-1.

Test procedure for mouthfeel and gastrointestinal tract irritation: 6 healthy volunteers, who had no bad habits such as smoking and drinking and had certain sensory evaluation practice, were enrolled. Each volunteer took a sample into his or her mouth and ingested it with warm water at 10:00 am every day, and recorded his or her actual feeling after 20 minutes. The tests were carried out for 6 consecutive days, and each volunteer took all samples one by one.

TABLE 4-1

Results of the mouthfeel and gastrointestinal tract irritation test for the porphyrin iron solid dispersions

| Samples | Mouthfeel | Feeling of stomach burning | Feeling of nausea |
|---|---|---|---|
| Formula 1-1 (porphyrin iron:Kollidon® VA 64 = 1:1) | Heavy bitterness, no other undesirable tastes | Slight stomach burning feeling | Slight nausea feeling |
| Formula 1-2 (porphyrin iron:Kollidon® VA 64 = 1:3) | Bitterness, heavy aftertaste, no other undesirable tastes | No obvious stomach burning feeling | No obvious nausea feeling |
| Formula 1-4 (porphyrin iron:Kollidon® VA 64 = 1:10) | Agglomerating in mouth, slight bitterness, no other undesirable tastes | No stomach burning feeling | No nausea feeling |
| Formula 2-2 (porphyrin iron:Soluplus® = 1:3) | Pleasant taste, no obvious undesirable tastes, good palatability | No stomach burning feeling | No nausea feeling |
| Formula 3-2 (porphyrin iron:HPMCAS = 1:3) | Obvious granular sensation in mouth, no obvious undesirable tastes | No obvious stomach burning feeling | No obvious nausea feeling |
| API | Heavy blood smell, undesirable tastes | Obvious stomach burning feeling | Obvious nausea feeling |

The results in Table 4-1 showed that by preparing porphyrin iron and Kollidon®VA 64, Soluplus® and HPMCAS into solid dispersions, the blood smell and undesirable tastes of porphyrin iron can be effectively masked and removed, and the stomach burning feeling and nausea feeling of porphyrin iron can be reduced significantly or even avoided, such that the compliance of patients can be improved.

What is claimed is:

1. A porphyrin iron solid dispersion, comprising porphyrin iron and a carrier material, wherein said carrier material is selected from one or more of polymers comprising vinylpyrrolidone units, or mixtures thereof; polymers comprising ethylene glycol units; and celluloses or cellulose esters; wherein porphyrin iron is dispersed in said carrier material at molecular level; and wherein the weight ratio of porphyrin iron to the carrier material is 1:1 to 1:10; and
wherein the porphyrin iron solid dispersion is prepared by a process including:
either feeding a homogenously mixed mixture of porphyrin iron and the carrier material at a said weight ratio, or simply feeding porphyrin iron and the carrier material at a said weight ratio, into a hot melt extruder preheated to about 120° C. to about 180° C.; and
cooling, pulverizing, and sieving the extruded mixture, to obtain the porphyrin iron solid dispersion.

2. The porphyrin iron solid dispersion according to claim 1, wherein said polymers comprising vinylpyrrolidone units, or mixtures thereof are selected from one or more of polyvinylpyrrolidone, a mixture of polyvinylpyrrolidone and polyvinyl acetate, and a copolymer of vinylpyrrolidone and vinyl acetate.

3. The porphyrin iron solid dispersion according to claim 1, wherein said polymers comprising vinylpyrrolidone units, or mixtures thereof have a K value of 10-95.

4. The porphyrin iron solid dispersion according to claim 2, wherein the weight ratio of polyvinylpyrrolidone and polyvinyl acetate in said mixture of polyvinylpyrrolidone and polyvinyl acetate is 1:9 to 9:1.

5. The porphyrin iron solid dispersion according to claim 2, wherein the weight ratio of vinylpyrrolidone units and vinyl acetate in said copolymer of vinylpyrrolidone and vinyl acetate is 1:9 to 9:1.

6. The porphyrin iron solid dispersion according to claim 1, wherein said polymers comprising ethylene glycol units are copolymers of polyethylene glycol/vinyl caprolactam/vinyl acetate.

7. The porphyrin iron solid dispersion according to claim 1, wherein said cellulose esters are hydroxypropylmethyl cellulose acetate succinate.

8. The porphyrin iron solid dispersion according to claim 7, wherein in said hydroxypropylmethyl cellulose acetate succinate, the content of the acetate group is 8 wt. % to 12 wt. %, and the content of the succinate group is 6 wt. % to 15 wt. %, based on the weight of said hydroxypropylmethyl cellulose acetate succinate.

9. The porphyrin iron solid dispersion according to claim 1, wherein the solid dispersion further comprises a pharmaceutically acceptable pharmaceutical adjuvant, and the process includes either feeding a homogenously mixed mixture of porphyrin iron and the carrier material and the pharmaceutically acceptable pharmaceutical adjuvant, or simply feeding porphyrin iron and the carrier material and the pharmaceutically acceptable pharmaceutical adjuvant, into the hot melt extruder.

10. A process of preparing a porphyrin iron solid dispersion comprising porphyrin iron dispersed in a carrier material at molecular level, the process including:
either feeding a homogenously mixed mixture of porphyrin iron and said carrier material at a weight ratio of 1:1-1:10, and an optional pharmaceutically acceptable pharmaceutical adjuvant, or simply feeding porphyrin iron and said carrier material at said weight ratio and an optional pharmaceutically acceptable pharmaceutical adjuvant, into a hot melt extruder preheated to about 120° C. to about 180° C.; and
cooling, pulverizing, and sieving the extruded mixture, to obtain the porphyrin iron solid dispersion;
wherein said carrier material is selected from one or more of polymers comprising vinylpyrrolidone units, or mixtures thereof; polymers comprising ethylene glycol units; and celluloses or cellulose esters.

11. A pharmaceutical composition comprising the porphyrin iron solid dispersion according to claim 1, wherein said pharmaceutical composition is in the form of powders, granules, pills, capsules or tablets.

12. A pharmaceutical composition according to claim 11, further comprising a pharmaceutically acceptable pharmaceutical adjuvant selected from one or more of surfactants, diluents, disintegrants, binders, and lubricants.

13. The porphyrin iron solid dispersion according to claim 2, wherein said polymers comprising vinylpyrrolidone units, or mixtures thereof have a K value of 10-95.

14. The porphyrin iron solid dispersion according to claim 1, wherein said polymers comprising vinylpyrrolidone units, or mixtures thereof have a K value of 25-70.

15. The porphyrin iron solid dispersion according to claim 2, wherein the weight ratio of polyvinylpyrrolidone and polyvinyl acetate in said mixture of polyvinylpyrrolidone and polyvinyl acetate is 2:8 to 8:2.

16. The porphyrin iron solid dispersion according to claim 2, wherein the weight ratio of vinylpyrrolidone units and vinyl acetate in said copolymer of vinylpyrrolidone and vinyl acetate is 4:6 to 6:4.

17. The porphyrin iron solid dispersion according to claim 1, wherein said celluloses or cellulose esters are selected from one or more of methyl cellulose, hydroxymethyl cellulose, hydroxylethyl cellulose, hydroxypropyl cellulose, hydroxyethyl methyl cellulose and hydroxypropylmethyl cellulose, carboxymethyl cellulose, sodium carboxymethyl cellulose, carboxymethyl ethyl cellulose, hydroxypropylmethyl cellulose acetate succinate, hydroxypropylmethyl cellulose phthalate, and cellulose acetate phthalate.

18. The porphyrin iron solid dispersion according to claim 1, wherein the weight ratio of porphyrin iron to the carrier material is 1:1 to 1:4.

19. The porphyrin iron solid dispersion according to claim 1, wherein the weight ratio of porphyrin iron to the carrier material is 1:1 to 1:3.

20. The process according to claim 10, wherein the porphyrin iron and the carrier material are at a weight ratio of 1:1-1:4.

21. The process according to claim 10, wherein the porphyrin iron and the carrier material are at a weight ratio of 1:1-1:3.

22. The porphyrin iron solid dispersion according to claim 2, wherein said polymers comprising vinylpyrrolidone units, or mixtures thereof have a K value of 25-70.

23. The porphyrin iron solid dispersion according to claim 9, wherein the pharmaceutically acceptable pharmaceutical adjuvant is selected from one or more of surfactants, diluents, disintegrants, binders, and lubricants.

* * * * *

UNITED STATES PATENT AND TRADEMARK OFFICE
CERTIFICATE OF CORRECTION

PATENT NO. : 10,391,103 B2
APPLICATION NO. : 15/033310
DATED : August 27, 2019
INVENTOR(S) : Larry Yun Fang et al.

Page 1 of 1

It is certified that error appears in the above-identified patent and that said Letters Patent is hereby corrected as shown below:

On the Title Page

Item (72) Inventors should read:
Jiansheng Wan, Shanghai (CN)
Kun Li, Shanghai (CN)
Maojian Gu, Shanghai (CN)

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*